United States Patent [19]
Thony et al.

[11] Patent Number: 5,892,586
[45] Date of Patent: Apr. 6, 1999

[54] REMOTE GAS DETECTION APPARATUS HAVING A MICROLASER

[75] Inventors: Philippe Thony; Engin Molva, both of Grenoble; Bernard Ferrand, Voreppe, all of France

[73] Assignee: Commissariat a l'Energie Atomique, Paris, France

[21] Appl. No.: 823,586

[22] Filed: Mar. 25, 1997

[30] Foreign Application Priority Data

Apr. 4, 1996 [FR] France ................................. 96 04242

[51] Int. Cl.$^6$ .......................... H01S 3/113; G01N 21/00
[52] U.S. Cl. ............................................... 356/437; 372/98
[58] Field of Search ................................. 356/434, 437; 250/338.5, 339.13; 372/98

[56] References Cited

U.S. PATENT DOCUMENTS

| | | | |
|---|---|---|---|
| 4,708,483 | 11/1987 | Lorenz | 356/376 |
| 5,015,099 | 5/1991 | Nagai et al. | 250/339.13 |
| 5,331,409 | 7/1994 | Thurtell et al. | 356/437 |
| 5,381,431 | 1/1995 | Zayhowski | 372/10 |
| 5,430,754 | 7/1995 | Suzuki et al. | 372/22 |
| 5,459,574 | 10/1995 | Lee et al. | 356/437 |
| 5,502,737 | 3/1996 | Chartier | 372/11 |
| 5,511,085 | 4/1996 | Marshall | 372/22 |

FOREIGN PATENT DOCUMENTS

| | | |
|---|---|---|
| 0653824 A1 | 5/1995 | European Pat. Off. . |
| 95 00767 | 1/1995 | France . |
| 2 734 093 | 5/1995 | France . |
| 4117072 A1 | 11/1992 | Germany . |

OTHER PUBLICATIONS

Shimose, et al., *Remote Sensing of Methane Gas by Differential Absorption Measurement Using a Wavelength Tunable DFB LD*, IEEE Photonics Technology Letters, vol. 3, No. 1, Jan. 1991, pp. 86–87.

Boyd, *Non–Linear Optics*, pp. 85–90.

Terry, et al., *Low–Threshold Operation of an All–Solid–State KTP Optical Parametric Oscillator*, Optical Society of America, vol. 11, No. 5, May 1994, pp. 758–769.

*Primary Examiner*—Frank G. Font
*Assistant Examiner*—Zandra V. Smith
*Attorney, Agent, or Firm*—Burns, Doane, Swecker & Mathis, LLP

[57] ABSTRACT

The invention relates to a remote gas detection process comprising: the emission of a first radiation (4), at at least one absorption wavelength for the gas to be detected, with the aid of a first switched microlaser, in the direction of a test area (6), the production of a first signal (S), representative of the radiation quantity scattered by said gas in response to the interaction between the molecules or atoms of said gas and said first radiation. The invention also relates to an apparatus for performing this process.

4 Claims, 4 Drawing Sheets

FIG. 10

# REMOTE GAS DETECTION APPARATUS HAVING A MICROLASER

TECHNICAL FIELD AND PRIOR ART

The invention relates to the field of the measurement by optical means of gases in the atmosphere. The detected gases are mixed with air in very small concentrations. They are often toxic, polluting or dangerous gases, such as e.g. methane, which is an explosive gas in air for a certain concentration.

The measurement principle consists of determining the absorption in an area of the atmosphere. The tested atmosphere area is illuminated by a light source, the light traversing said area. The light signal is recovered by any arbitrary means. This signal is quantified on a detector, which gives information on the light quantity transmitted and absorbed in the tested area. Moreover, the gases liable to exist in the tested area are known and characterized from the spectroscopy standpoint, their absorption spectrum being known. The measurement makes it possible to recognize the gas or its presence as a function of the characteristics of the illumination source.

To within a few variants, this absorption principle is implemented in two apparatus types:

Spectrometers, which use a wide spectrum light source. They give information on the spectrum of chemical species measured on a wide wavelength range (from 3 to 5 or 8 to 13 $\mu$m for e.g. Fourier transform infrared spectrometers). The measured spectrum is then interpreted in order to identity the detected chemical species.

Apparatuses a narrow spectrum source. These sources (e.g. a laser) consequently emit at a precise wavelength. These apparatuses measure the absorption due to a previously identified chemical species. These measurements can be performed over a considerable distance. More specifically, the apparatuses of interest here belong to the second category.

The article by A. Tebo entitled "Optical monitoring techniques trace toxic pollutants", published in O.E. Reports, describes several polluting gas measuring methods. One of these methods is called DIAL (Differential Absorption Lidar) and uses a dye laser pumped by a neodymium (Nd)-doped YAG laser or by an excimer laser. The beam obtained at the dye outlet is frequency doubled. This apparatus uses high laser energies of approximately 1 mJ (millijoule) per pulse. It is suitable for measurements at very great distances of several hundred meters or several kilometres.

The article by J. P. WOLF entitled "3-D Monitoring of Air Pollution Using Mobile "All-solid-state" Lidar Systems" published in Optics and Photonics News, Jan. *1995, pp 27–29* describes a lamp-pumped Ti:Al$_2$O$_3$ (titanium-sapphire) laser means. The beam obtained at the output is frequency-doubled or pumps an optical parametric oscillator (OPO). This apparatus also uses high laser energies of a few dozen mJ per pulse. There again it is an apparatus suitable for measurements at very great distances of several kilometres.

However, certain applications require a measurement in a distance range between 5 and 50 m. This is the case when it is wished to detect a possible gas leak in the vicinity of an apparatus or when it is e.g. wished to monitor the methane concentration of a work site. In practice, the apparatuses described in the A. Tebo and J. P. Wolf articles are then inappropriate. Moreover, the prior art apparatuses do not have a flexible use.

In the case of the apparatus described by A. Tebo, a first given dye admittedly makes it possible to obtain a laser emission in a certain wavelength range appropriate for one or more given gases, but it is not suitable for other gases. Thus, for the latter it is necessary to find a second suitable dye (which is not always possible) and then replace the first dye by the second, which is difficult to carry out in certain measurement sites. For example, the problem arises of being able to detect compounds as different as oxygen, methane, ammonia, nitrogen dioxide and ozone. The first has a characteristic wavelength at 0.76 $\mu$m, the second at 1.54 $\mu$m, the third at 6.4 $\mu$m and the last at 9.5 $\mu$m. Under these conditions, several dyes are necessary, because a single would not be able to cover the entire frequency range from 0.5 to 10 $\mu$m.

The apparatus described by J. P. Wolf makes it possible to cover the spectral range 695 to 950 nm and the ranges 1.01 to 1.43 $\mu$m and 2.16 to 3.31 $\mu$m with an OPO.

However, this apparatus involves the use of a complex titanium-sapphire laser. The addition of a possible frequency doubler crystal or an OPO crystal is itself a problem. For the other wavelengths, which it is not possible to reach with a titanium-sapphire laser version incorporating a doubler or an OPO, it is necessary to use another laser, the titanium-sapphire laser being itself complicated and complex.

DESCRIPTION OF THE INVENTION

The problem is therefore to find another apparatus and another measuring process, making it possible to carry out medium distance measurements and which can easily be adapted to different wavelengths. To this end, the invention relates to a remote gas detection process comprising:

the emission of a first radiation, at at least one absorption wavelength for the gas to be detected, with the aid of a first switched microlaser, in the direction of a test area, the production of a first signal, representative of the radiation quantity scattered by said gas, in response to the interaction between the molecules or atoms of said gas and the first radiation.

This process can be easily carried out for detecting gases at a distance of a few dozen meters (e.g. between 5 and 40 m), despite the low energy levels of the beam of a microlaser (small number of photons per pulse).

A user can also easily have a complete series of microlasers, whose characteristics (in particular the composition of the active laser medium) make it possible to obtain emissions at different wavelengths. Thus, such a "battery" of microlasers makes it possible to carry out tests in a given area in situ and in a quasi-immediate manner, in order to determine there the presence of a particular target gas. An array of microlasers can also be installed in linear or matrix form, so that the operator has a wavelength "kit". This cannot be attained with an apparatus like that described in either the A. Tebo or the J. P. Wolf article.

The selectivity of the detection system according to the invention can be further increased by choosing a microlaser, whose geometrical parameters (length) with respect to the cavity make it possible to obtain a given emission spectrum. It is consequently possible to reduce the length of the microlaser or rather the Fabry-Perot resonant cavity, so as to be able to obtain a longitudinal monomode operation characterized by a single emitted line with a width of a few kilohertz.

It is also possible to dimension the microlaser for forming a longitudinal multimode spectrum, whose free spectral range is adapted to the spectrum of the vibrational lines of the gaseous molecules. This makes it possible to detect the fine structure (vibrational line) of the target gas and to better identify it.

Thus, the absorption of the light signal by the gas increases with the greater correspondence between the spectrum of the incident beam with the absorption spectrum of the gaseous species. The emission spectrum can optionally then be adjusted, e.g. by regulating the microlaser temperature. Thus, in both cases, the system selectivity is increased.

These possibilities of choosing or dimensioning the radiation source in order to obtain a given emission spectrum are difficult to achieve in the case of a tool like that described in the aforementioned articles by A. Tebo and J. P. Wolf.

Microlasers also have the advantage of having a very small size, the volume of a microlaser being approximately 1 mm$^3$ or less. The apparatus used for performing the process according to the invention is consequently small and easily transportable between individual measuring sites.

Advantageously, the process according to the invention also comprises:
the emission of pulses of a second radiation, in the direction of the test area, at a wavelength not absorbed by the gas to be detected,
the production of a second signal, representative of the radiation quantity scattered by said gas, in response to the interaction between the molecules or atoms of said gas and the second radiation.

For example, the second radiation can be produced by a second switched microlaser, which is compatible with the small size of microlasers.

The first and second radiations can also be emitted at two different wavelengths by the same microlaser, so that the apparatus would then be even more compact. For example, it is possible to use two longitudinal modes of the same microlaser, frequency spaced by $$n\frac{C}{2L} \ (n \text{ integer} > 1), \frac{C}{2L}$$

representing the free spectral range of the microlaser cavity.

According to another example, the spectral emission characteristic of the microlaser undergoes time modulation and the two radiations are then obtained at consecutive times. It is then possible to then have a demodulation of the first and/or second signal.

In all cases, there can also be a stage of calculating the gas quantity or concentration on the basis of the first signal, or the first and second signals.

The first microlaser can be switched in passive manner by a saturable absorbent. The active medium of the microlaser is constituted by a base material (YAG, YLF, glass) doped with ions ensuring the laser effect ($Nd^{3+}$, $Cr^{4+}$, $Er^{3+}$, ...). The saturable absorbent is then advantageously made from the same base material and doped with ions giving it saturable absorbent properties. However, the ion pair retained for the active medium and the saturable absorbent is preferably adjusted to the gas to be detected. Thus, the invention also relates to the implementation of pairs of specific materials for the active laser medium and the saturable absorbent, suitable for the detection of certain gas species to be detected, such as methane or oxygen or carbon monoxide.

The invention also relates to an apparatus for performing the process according to the invention.

BRIEF DESCRIPTION OF THE DRAWINGS

The features and advantages of the invention can be better gathered from the following description of non-limitative embodiments and with reference to the attached drawings, wherein show.

DETAILED DESCRIPTION OF EMBODIMENTS OF THE INVENTION

Figure 1:
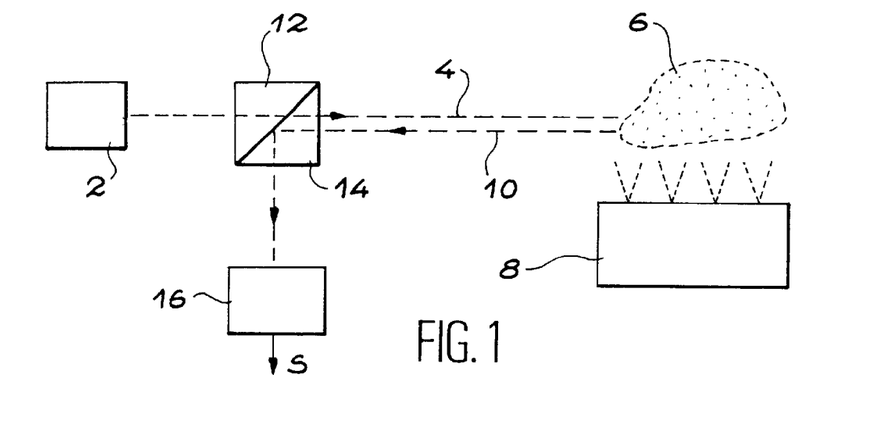
FIG. 1 Diagrammatically an embodiment of the invention.

FIG. 1 shows a first embodiment of the invention. In FIG. 1, a switched microlaser 2 delivers pulses of a beam 4 in the direction of an area 6 in which can optionally be located a gas to be detected, e.g. a noxious gas escaping from an object 8. The object 8 can e.g. be an apparatus, more particularly an electrical apparatus. The gas can e.g. be methane, which is explosive as from a certain concentration and whose presence causes safety and detection problems, especially in confined atmospheres (more particularly in the chemical industry and in mine galleries or levels).

At least one of the radiation wavelengths 4 emitted by the microlaser 2 is within an absorption line of the gas to be detected. If said gas is absent from the area 6, the radiation 4 traverses it without being absorbed. If said gas is present, it absorbs part of the photons of the radiation 4 and reemits a radiation known as back-scattered radiation 10. FIG. 1 only shows that part of the back-scattered radiation directed towards a beam splitter 12, which supplies said radiation to a detector 16, such as a semiconductor detector. Optionally, a filter can be placed between the prism 12 and the detector 16. The said detector produces a signal representative of the radiation quantity back-scattered by the gas present in the area 6 and therefore representative of the quantity or concentration of said gas. The signal S can then be supplied to a unit for processing the signal permitting a calculation of the sought characteristic of the gas. The calculated value can then e.g. be displayed by a display means and can also be stored for subsequent processing with other stored values.

The aforementioned apparatus is particularly suitable for carrying out gas detection at a distance between 5 and 40 or 50 m, e.g. at approximately 30 m. Distances of approximately 200 m can be reached with certain microlasers (particularly YAG:Nd).

The microlaser 2 has an active medium between two mirrors, which seal a microlaser cavity. The material constituting the active medium is essentially a base material doped with an active ion. The base material can e.g. be chosen from among the following materials: YAG ($Y_3Al_5O_{12}$), YSO ($Y_2SiO_5$), YLF ($YLiF_4$). In all cases, the doping ion can e.g. be neodymium ($Nd^{3+}$), erbium ($Er^{3+}$) or chromium ($Cr^{4+}$). The base material can also be glass or silica, e.g. doped with erbium ($Er^{3+}$).

The active medium of a microlaser has a limited thickness (between 150 and 1000 $\mu$m) and a small size (a few mm ). The cavity mirrors can be directly deposited above. Finally, it can be pumped by a laser diode, e.g. III–V, directly hybridized on the microlaser or coupled to the latter by an optical fibre. The microlaser is an actively or passively switched microlaser.

Figure 2:
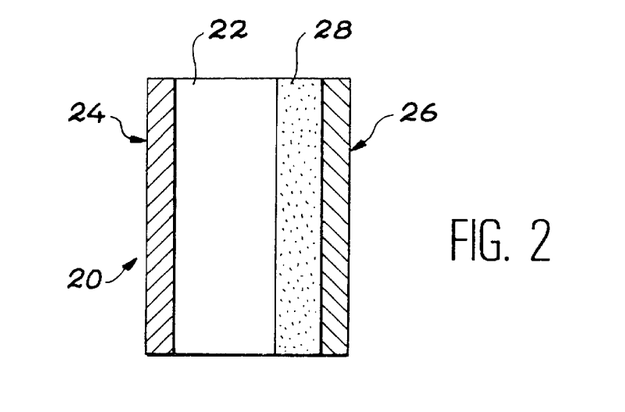
FIG. 2 A diagrammatic representation of a microlaser with intracavity saturable absorbent.

In the case of a passively switched microlaser, use is made of the properties of saturable absorbents. These materials are highly absorbent at a certain laser wavelength and at a low power density and become virtually transparent when the power density exceeds a certain threshold, which is called the saturation intensity. The saturable absorbent introduces time-variable losses, which prevent the laser effect for a certain time during which the pumping energy is stored in the excited level of the gain material. These losses are suddenly decreased when the power density reaches the saturation intensity, thus releasing the stored energy in a very short time. This gives a pulse having a very high peak power. Preferably, the saturable absorbent material is located within the microlaser cavity. Such a structure is illustrated in FIG. 2, where the reference 20 designates the microlaser cavity, which has an active laser material 22 and two microlaser cavity input and output mirrors 24, 26. A saturable absorbent 28 is located within the cavity and can be deposited in thin film form directly on the solid active material 22. Such a structure is described in EP-653 824 (U.S. Pat. No. 5,495,494). In said reference can also be found all information relative to the process for producing this structure. In particular the liquid phase epitaxy method for the direct deposition on the active laser material is well suited to producing saturable absorbents of the type given in exemplified manner hereinafter.

In the case of a base material of the glass or silica type, preparation also involves a stage of melting said material, followed by a solidification stage. Finally, material sections are cut up to the desired thickness. The following stages are identical to those described in EP-653 824.

Figure 3:
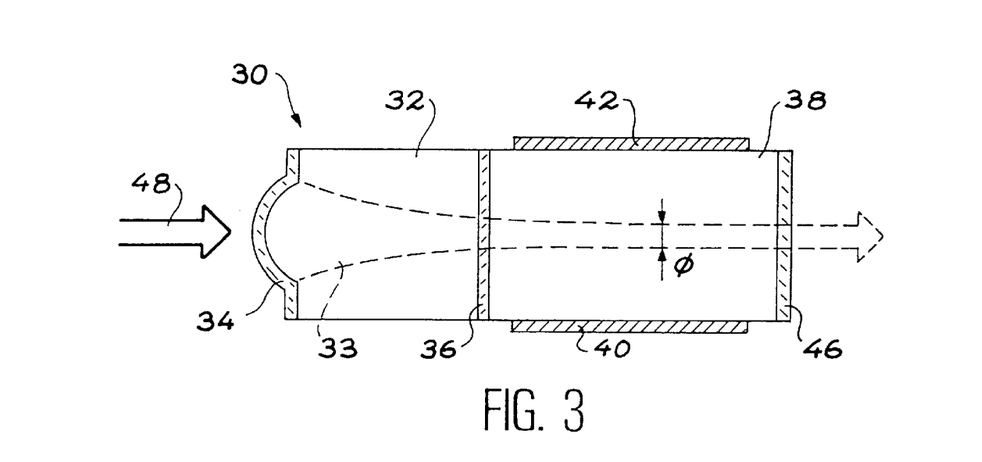
FIG. 3 An actively switched microlaser.

According to another variant, active switching of the microlaser can take place. As hereinbefore, active switching consists of again adding time-variable losses within the cavity, but on this occasion the value of the losses is externally controlled by the user. Use is e.g. made of an intracavity acousto-optical or electro-optical material. The storage time, the cavity opening time and the repetition rate can be chosen independently by the user. However, this requires switching-adapted electronics. An actively switched solid microlaser structure implementable within the scope of the invention is illustrated in FIG. 3, where reference 30 designates the microlaser cavity. This apparatus has a first resonant cavity between a first input mirror 34 and an intermediate mirror 36 and within which is incorporated the active laser material 32. It has a second resonant cavity between the intermediate mirror 36 and an output mirror 46, within which is located a material 38, whose optical index is suitable for modulation by an external interference or disturbance. An example of such a material is an electro-optical material controlled by an external voltage pulse applied with the aid of electrodes 40, 42 located on either side of the electro-optical material 38. Advantageously, means are located at the entrance of the first cavity to reduce the size of the laser beam. These means can be constituted by a concave mirror produced with a micromirror on the face of the active laser material 32 to be traversed by the pumping beam. Details of such a structure, its variants and the corresponding production processes are given in FR-A-95 00767, filed on Jan. 24, 1995 and whose complete content is incorporated by reference into the present description.

Figure 4:
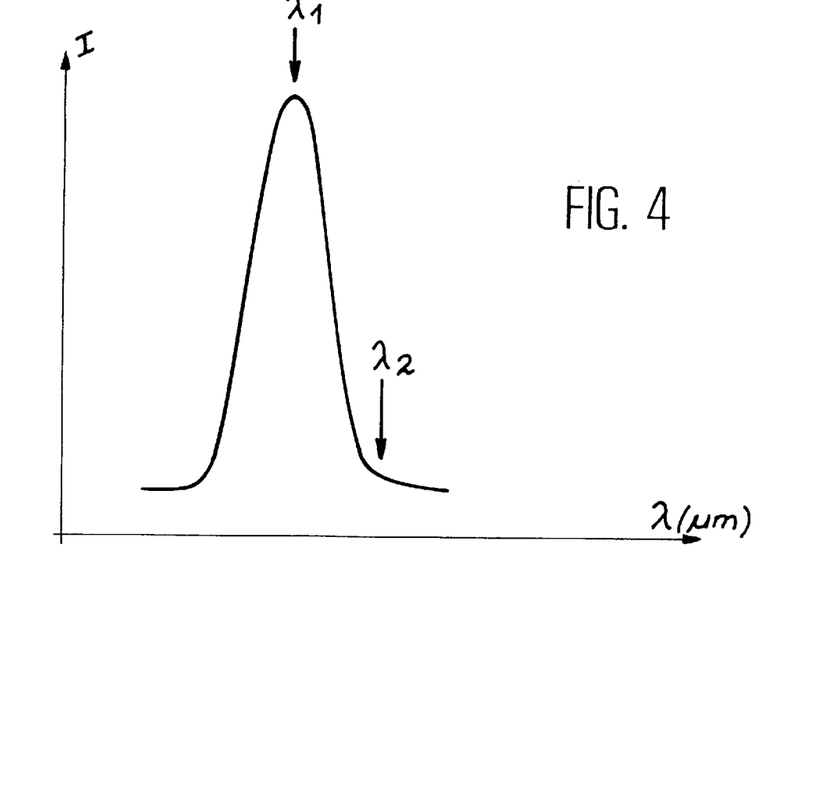
FIG. 4 A spectrum of an absorption line of a gas to be detected.

Another embodiment of the invention will now be described, its principle being explained with the aid of FIG. 4. FIG. 4 shows part of the absorption spectrum (absorption peak 50) of a gas to be detected. As stated hereinbefore, a detection process consists of directing towards the gas to be detected a radiation, whose wavelength $\lambda_1$ is within such an absorption peak characteristic for the gas in question. According to a variant, a second radiation is emitted at a wavelength $\lambda_2$ e.g. at the foot of the absorption line 50. A gas possibly present in a test area, such as area 6 of FIG. 1, back-scatters the two wavelengths towards the system detector 16. Thus, the latter supplies two signals $S_1$ and $S_2$:$S_1$ being representative of the back-scattered radiation quantity resulting from the interaction between the molecules or atoms of the gas to be detected and the radiation at length $\lambda_1$, $S_2$ representing the back-scattered radiation quantity resulting from the interaction between the molecules or atoms of the gas to be detected and the radiation at the wavelength $\lambda_2$. The signals $S_1$ and $S_2$ can then be stored for subsequent processing, or analysis means can permit an in situ determination. In all cases, a processing can consists of forming the difference of the signals $S_1$–$S_2$. The radiation $\lambda_2$ supplies a reference which is virtually independent of the presence or the concentration of the gas to be detected and with respect to said reference the signal $S_1$ represents the concentration and/or quantity variations of the gas to be detected.

An apparatus for obtaining two emissions of radiations at separate wavelengths can e.g. have two microlaser sources, with two juxtaposed microlaser cavities, each being pumped independently of the other by optical means. The very small size of the microlasers permits such a juxtapositioning without greatly modifying the final volume of the apparatus. The two microlaser cavities are then such that they emit at wavelengths which are slightly mutually displaced.

Figure 5:
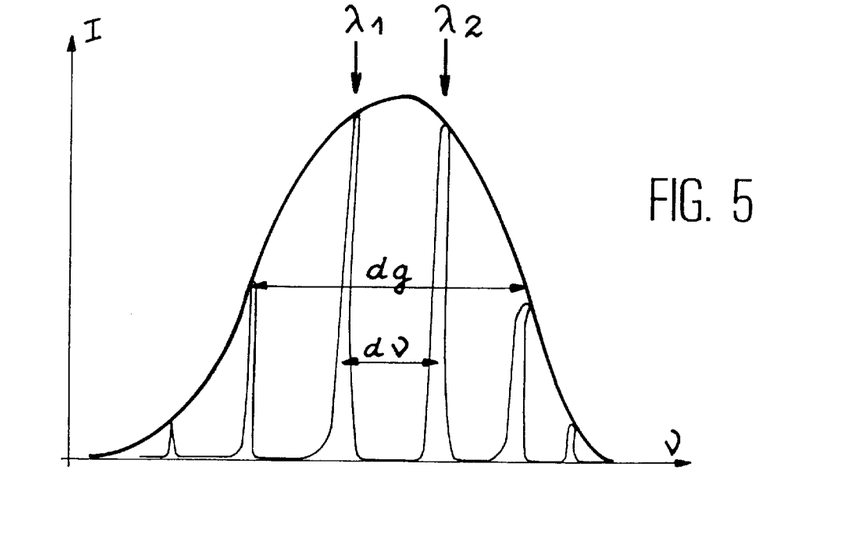
FIG. 5 The distribution of modes in a planar-planar Fabry-Peroc cavity.

It is also possible to use a single microlaser source emitting two wavelengths. Thus, laser materials exist, which can simultaneously emit two close wavelengths under certain conditions (e.g. ytterbium-doped YAG). Another possibility consists of making use of the fact that a microlaser cavity can emit several longitudinal modes. FIG. 5 shows a diagram of the spectral distribution of the Fabry-Perot modes of the amplifier medium. In this diagram, the envelope of modes represents the gain band, dg represents the width of the gain band and dv the spacing of the modes. On the vertical axis is plotted the intensity in arbitrary units. The horizontal axis is a frequency scale. If the Fabry-Perot cavity is a planar-planar cavity of optical thickness e, the free spectral range dv between two modes is given by: $dv=c/2e$, in which c is the speed of light.

If dg is the width of the gain band (laser emission) of the material, the number of modes N will be given by:$N=dg/dv$.

It can be seen that the number of modes within the cavity essentially depends on the thickness of the latter. It can therefore be chosen in such a way that said number N is e.g. equal to 2. Then two emissions are obtained at two wavelengths $\lambda 1$ and $\lambda 2$, which are slightly mutually displaced by a quantity $dv=c/2e$.

It is also possible to choose e so as to obtain N=1. The typical thickness of a YAG active medium microlaser cavity without any intracavity switching means making it possible to obtain N=1 is approximately 750 $\mu$m. With intracavity switching means, account must also be taken of the optical thickness thereof.

According to yet another variant, means are provided, which make it possible to carry out a time modulation of the microlaser emission spectrum. These means can e.g. be an intracavity electro-optical crystal or microlaser temperature modulation means. It is then possible to have a processing of the signal incorporating a demodulation of the measured signal or signals.

In all cases, the emission wavelength or wavelengths of the microlaser are essentially dependent on the characteristics of the active laser medium, i.e. its composition and, in the case where switching takes place with the aid of a saturable absorbent, the nature of the latter, i.e. its composition.

For example, for a neodymium-doped active laser medium, the obtainable wavelengths are around 1.06 μm, 1.32 μm or 946 nm. As a function of the matrixes in which the neodymium ion is inserted, said values vary slightly. Other dopants permit emissions at other wavelengths: thulium (emission at approximately 1.9 μm), and holmium (emission at approximately 2.1 μm and 3.9 μm), erbium (emission at 1.5 μm and approximately 3 μm), ytterbium (emission at approximately 1 μm) and praseodymium (emission at approximately 5.2 and 7.2 μm).

When there is an intracavity saturable absorbent, the latter is preferably formed by a base material of the same type as the base material of the active laser medium and is doped with ions giving it saturable absorbent properties. Thus, the microlaser cavity then has two elements constituted by the same base material doped with different ions, which defines an ion pair for the same base material, the assembly determining the emission wavelength of the microlaser cavity. As a function of the absorption wavelength of the gas to be detected, chosen so as to identify the latter (e.g. wavelength $\lambda_1$ of the absorption peak 50 of FIG. 4), are then chosen the base material and the ion pair.

Thus, for a certain number of gaseous compounds to be detected, the following table I gives a value of an absorption wavelength, the doping ion pair for the laser medium and the saturable absorbent. The base material of these two elements is, in the first three cases, YAG and, in the last two cases, glass or silica.

TABLE I

| Compound to be detected | Formula | Absorption wavelength | Doping ion (laser medium) | Doping ion (saturable absorbent) |
|---|---|---|---|---|
| Methane, propane, butane | $CH_4$ $C_3H_8$ $C_4H_{10}$ | 1.33 μm | neodymium | vanadium |
| Hydrofluoric acid | HF | 1.33 μm | neodymium | vanadium |
| Water vapour | $H_2O$ | 1.36 μm | neodymium or chromium | vanadium |
| Carbon oxides | Co or $CO_2$ | 1.57 μm | erbium | uranium or erbium |
| Ammonia | $NH_3$ | 1.54 μm | erbium | uranium or erbium |

For these 5 compounds, an InGaAs or germanium-based semiconductor detector is able to detect the radiation back-scattered by the gaseous compound.

In all cases, no matter whether switching is active or passive, it is possible to combine a microlaser structure emitting at a given wavelength with a non-linear and preferably intracavity element, such as an optical parametric oscillator (OPO) or a frequency doubler or tripler crystal, or an optical parametric amplifier OPA), or a device making an optical frequency sum or difference (KTP or $LiNbO_3$ or $KNbO_3$ or BBO or LB) or a device effecting a Raman frequency shift. These devices make it possible to obtain wavelengths appropriate for the gaseous species to be detected.

In particular, for revealing plant aerosols, whose absorption wavelengths are between 250 and 350 nm, use is preferably made with a frequency tripled or quadrupled, neodymium-doped YAG laser material. In the case of a passive switching, the saturable absorbent will then preferably be YAG doped with $Cr^{4+}$ chromium ions.

Figure 9:
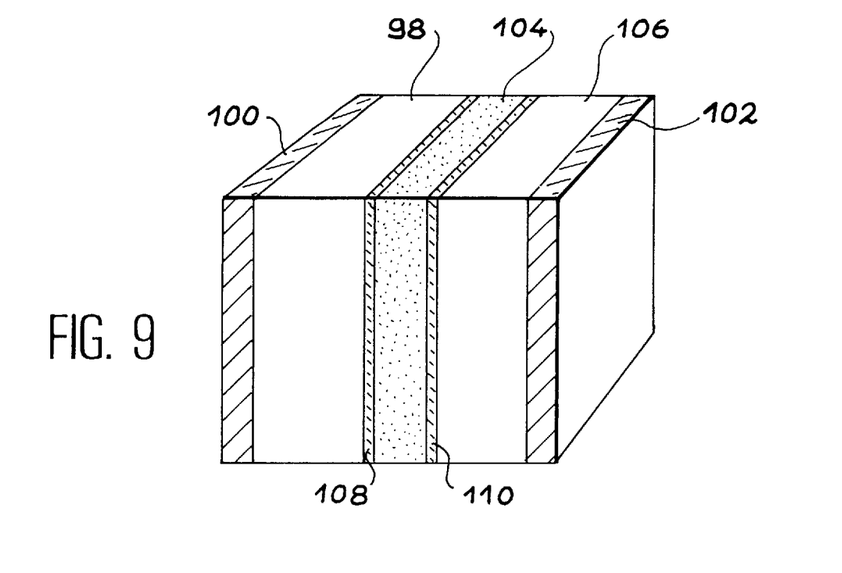
FIGS. 9 & 10 Configurations of a switched microlaser with nonlinear intracavity material.

A microlaser structure incorporating an active switching element and an optically non-linear element is shown in FIG. 9. More specifically, the cavity has an active laser medium 98, sealed by an input mirror 100 and an output mirror 102. In addition, within the cavity there are two other elements, namely an active or passive cavity switching element 104 and an non-linear material 106 making it possible to multiply by a factor n (n>2) the base frequency of the active laser medium 98.

The non-linear material can e.g. be a non-linear KTP crystal making it possible to obtain a microlaser base frequency doubling. For example, a radiation at 1064 nm obtained from a YAG:Nd active laser medium is converted by said crystal into radiation at 532 nm. A frequency quadrupling effect can be obtained by incorporating within said same microlaser cavity a non-linear KTP crystal and a non-linear BBO crystal. The invention also applies to any non-linear crystal type making it possible to double the frequency of the active laser medium of the microcavity, as well as any other non-linear crystal permitting the multiplication of the frequency of the laser medium of the microcavity by a factor n (n>2, e.g. n=3, 4, etc.). For example, use can be made of the following crystals: BBO, LBO, $KNbO_3$, $LiNbO_3$.

The simultaneous presence within the microlaser cavity of switching means 104 for the same and means 106 for multiplying the base frequency of the active laser medium leads to a very marked increase in the operating efficiency of the means (crystal 106) permitting the frequency to be multiplied. Thus, for a doubler crystal, an efficiency of 80% has been noted with this structure.

As illustrated in FIG. 9, other additional elements can be included in the cavity, such as e.g. an adhesive layer 108 permitting the connection of the saturable absorbent 104 to the active laser medium 98, or a layer 110 of a medium making it possible to adapt the index at the interface of the media 106 and 104.

Figure 10:
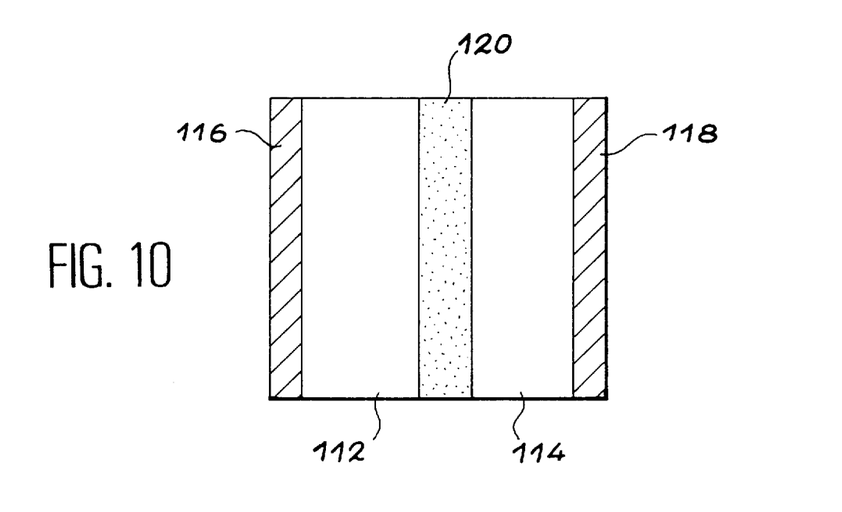

FIG. 10 shows the microlaser obtained when the saturable absorbent 120 is in the form of a thin film directly deposited on the active laser medium 112. The non-linear material 114 completes the microlaser cavity, limited by the mirrors 116, 118.

The processes for the production of these structures with a non-linear intracavity element are described in FR-A-95 05650.

In the case of oxygen ($O_2$) detection, the chosen absorption wavelength is around 0.76 um. The active laser material is preferably based on silicon or glass doped with erbium ions and frequency doubled, whilst the saturable absorbent is also based on silicon or glass doped with uranium or erbium ions. A silicon detector then makes it possible to detect the back-scattered radiation.

In order to achieve higher wavelengths, e.g. between 3 and 10 μm, use can be made of an optical parametric oscillator. By bringing about an interaction between the laser beam and an OPO crystal, the OPO makes it possible to generate a radiation with a higher wavelength than that of the laser, whose space and time characteristics are close to those of the pumping beam. By modifying the phase tuning conditions of the non-linear crystal (either by rotating the crystal, or by changing the temperature), it is possible to continuously vary within a very wide range the wavelength of the emitted radiation. More specifically, a pumping photon of frequency $\cup_p$ is broken down, at the OPO output, into two photons, namely the highest frequency photon $\cup_s$ is called the "signal" photon and the lower frequency photon $\cup_i$ is called the "idler" photon. For energy conservation reasons, the relation: $\cup_s + \cup_i = \cup_p$ is used. FR-A-95 05654, filed on May 12, 1995, describes OPO structures pumped by a microlaser and which are compatible with the present invention.

Figure 6:
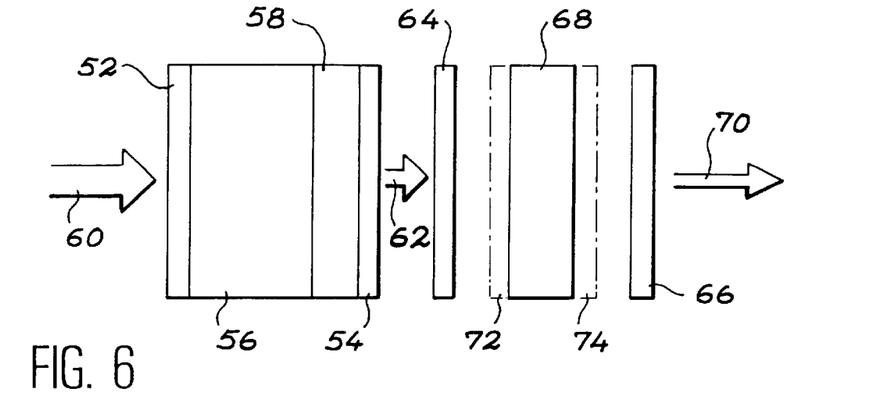
FIGS. 6 to 8 Various microlaser-pumped OPO configurations.
Figure 7:
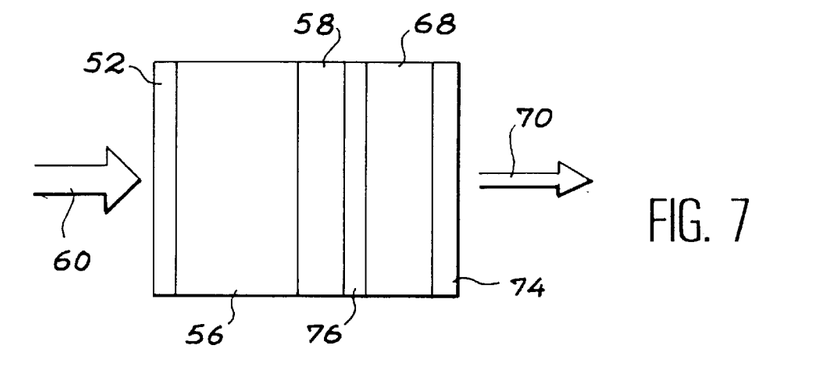
Figure 8:
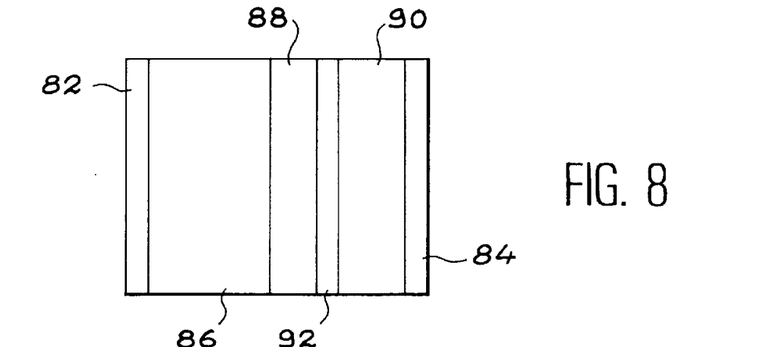

FIGS. 6 to 8 show different possible OPO-pumping microlaser structures.

In FIG. 6, references 52 and 54 designate input and output mirrors of a microlaser cavity having an active laser medium 56 and means 58 for the active or passive switching of said cavity. The cavity can be pumped by means not shown in the drawing, the pumping beam being designated 60. The cavity emits a laser beam 62, which will in turn pump a second cavity, known as the OPO cavity. The latter is defined by two mirrors 64, 66 between which is placed a nonlinear material 68 (e.g. a crystal) making it possible to obtain an OPO cavity, which in turn emits an OPO beam 70.

The constituent material of the medium 68 can be chosen from among known non-linear materials, such as e.g. $KTiOPO_4$ (KTP), $MgO:LiNbO_3$, $\beta\text{-}aB_2O_4$, $LiB_3O_5$, and AgGaSe. The properties of KTP are e.g. described in the article by Terry et al, published in Journal of Optical Society of America, B, vol. 11, pp 758–769, 1994. The properties of other non-linear materials making it possible to obtain an OPO are described in the work by R. W. Boyd entitled "Non-linear optics", Academic Press, 1992, USa, ISBN 0-12-121680-2, particularly pp 85 ff. The input and output mirrors of the OPO cavity can also be arranged in the manner shown in dotted line form in FIG. 6. In this case two mirrors 72, 74 are directly deposited on the input and output faces of the material 68. This configuration leads to greater compactness and gives a foolproof cavity, which does not have to be aligned during operation.

As a result of the pumping by a microlaser, it is possible not only to lower the OPO cavity threshold energy, but also reduce the length of the crystal 68 necessary for OPO operation. Thus, in the article by Terry et al referred to hereinbefore, a description is given of an OPO with a 20 mm long crystal, whilst the invention makes it possible to use materials a few mm thick, e.g. 5 mm. In general terms, as a result of the properties of the beam 62 emitted by the laser, this result (lowered threshold energy, reduced crystal length) applies not only to a KTP crystal, but also to any other non-linear material or crystal used for producing an OPO cavity.

The compactness of the system is further increased if, as illustrated in FIG. 7, mirrors 54 and 64 coincide. The structure obtained is then extremely compact. In FIG. 7 elements identical to those of FIG. 6 are given the same references and 76 designates an intermediate mirror common to the microlaser cavity and the OPO cavity. As the microlaser cavity is itself very compact, even with a switching element 58, it is thus possible to obtain an OPO, whose total length, including its pumping means, does not exceed 6 mm for a section of 1 $mm^2$, i.e. a total volume of 6 $mm^3$.

In addition, all the OPO structures described hereinbefore benefit greatly from the collective production possibilities for microlasers. Moreover, direct mirror deposition on the non-linear material 68 is also compatible with collective production procedures and consequently the complete apparatus is compatible with collective methods used in microelectronics. Therefore mass production can take place at very low cost.

The input mirror 52 deposited by known processes is preferably a dichroic mirror having a maximum reflectivity (as close as possible to 100%) at the laser wavelength and the highest possible transmission (>80%) at the pumping wavelength (generally about 800 nm for Nd-doped materials, 980 nm for Er-doped materials and 78 nm for Tm-doped materials). The output mirror 54, 76 is also preferably dichroic, but allows the passage of a few per cent of the laser beam.

With regards to the OPO cavity, it is possible to adjust the reflectivities of the input and output mirrors of said cavity so as to form a doubly resonant cavity around the non-linear material 68. The input mirror 76 has a high reflectivity close to 100% at the $\lambda_{signal}$ for a single resonant cavity and a reflectivity close to 100% $\lambda_{idler}$ for a double resonant cavity. The output mirror 76, 66 has a reflectivity higher than 90% for $\lambda_{signal}$ for a single resonant cavity or $\lambda_{idler}$ for a double resonant cavity. This permits a further reduction in the operating threshold of the cavity 68.

Another embodiment is illustrated in FIG. 8. On this occasion there are no longer two separate cavities (microlaser cavity and OPO cavity), but instead a microlaser cavity containing the OPO cavity. The microlaser cavity is defined by two input and output mirrors 82, 84 of the microlaser cavity and contains an active laser medium 86, a cavity switching element 88, a non-linear crystal 90 forming with an intermediate mirror 92 and the output mirror 84 of the cavity, an OPO "subcavity". To this end, the intermediate mirror 92 is transparent at the wavelength of the laser beam and reflecting at the wavelength of the signal beam of the OPO cavity, whilst the mirror 84 is transparent to $\lambda_{idler}$ for a single resonant cavity and reflecting at $\lambda_{idler}$ for a double resonant cavity. The mirror 84 is partly transparent at the wavelength of the signal beam of the OPO cavity. This embodiment makes it possible to have an even higher energy density within the OPO cavity, whilst retaining the benefit of an extremely compact and monolithic structure.

The processes for producing these structures with OPO are described in FR-A-95 05654.

Using an OPO, according to one of the structures described hereinbefore relative to FIGS. 6 to 8, it is in particular possible to generate radiation at a wavelength of 3.3 μm suitable for revealing benzene ($C_6H_6$) vapours. In combination with an OPO, a microlaser emitting at 1.06 μm (e.g. YAG:Nd) makes it possible to emit wavelengths of 1.5 and 3.3 μm. Moreover, these two wavelengths can be used for detecting one or two gases. An InSB or InAs-based semiconductor detector is suitable for detecting a signal back-scattered from a benzene vapour.

Nitrogen dioxide ($NO_2$) has an absorption wavelength at 6.4 μm. Here again, this wavelength can be reached with a microlaser (YAG: $Nd^{3+}$, satsurable absorbent=YAG:$Cr^{4+}$), which pumps an OPO ($AgGaSe_2$). An InSb-based semiconductor detector makes it possible to detect the back-scattered radiation.

Ozone has an absorption peak at approximately 9.5 μm. An OPO ($AgGaSe_2$) pumped by a microlaser (YAG:Tm, saturable absorbent=YAG:$Ho^{3+}$) makes it possible to obtain a radiation at this wavelength. A HgCdTe-based detector permits a detection at said wavelength.

In all cases, no matter what the switching mode and the structure of the microlaser cavity adopted, it is possible to obtain a planar—planar cavity, in which the input and output mirrors are planar. According to another embodiment, it is also possible to obtain a stable cavity with concave micromirrors at the input and/or output of the microlaser cavity. The presence of at least one concave mirror makes it possible to stabilize the cavity, which then has a lower switching threshold and a higher efficiency. Moreover, the presence of a concave micromirror makes it possible to adjust the size of the laser beam in the different media of the cavity, which again increases the power density at the different intracavity elements (non-linear OPO element, saturable absorbent). In the case of active switching (FIG. 3), the presence of a concave micromirror at the input makes it possible to reduce the voltage to be applied on either side of the active element 38. Without an active mirror it would be necessary to use a voltage of approximately 1000 V, whereas the mirror reduces said voltage to approximately 100 V.

The process and apparatus according to the invention offer numerous advantages and in particular those linked with the microlaser structure. The microlaser has a reduced cost, it being mass producible and pumped by a laser diode. It is also a very reliable apparatus, due to its monolithic, foolproof nature. A microlaser requires no maintenance and no settings, the system being compact and easily transportable. Finally, the power consumption necessary for operation is very low.

We claim:

1. Remote oxygen detection process comprising:
   the emission of a first radiation, at at least one absorption wavelength ($\lambda_1$) of oxygen, with the aid of a first switched frequency doubled microlaser, in the direction of a test area, said first switched frequency doubled microlaser being passively switched with the aid of a saturable absorbent, and having an active laser medium constituted by silica or glass doped with erbium ions, the saturable absorbent being constituted by silica or glass doped with uranium (U) ions or erbium (Er) ions,
   the production of a first signal, representative of a radiation quantity scattered by said oxygen, in response to the interaction between the molecules or atoms of said oxygen and the first radiation.

2. Remote plant aerosol detection process comprising:
   the emission of a first radiation, at at least one absorption wavelength ($\lambda_1$) of the plant aerosol to be detected, with the aid of a first switched frequency tripled or quadrupled microlaser, in the direction of a test area, said first switched frequency tripled or quadrupled microlaser being passively switched with the aid of a saturable absorbent, and having an active laser medium constituted by YAG doped with neodymium (Nd) or chromium (Cr) or thulium (Tm), the saturable absorbent being constituted by YAG doped with vanadium or holmium (Ho) or chromium,
   the production of a first signal, representative of a radiation quantity scattered by said plant aerosol, in response to the interaction between the molecules or atoms of said plant aerosol and the first radiation.

3. Remote gas detection apparatus comprising:
   a first frequency doubled switched microlaser emitting a first radiation at a first wavelength ($\lambda_1$), comprising a saturable absorbent for passively switching the microlaser, and having an active laser medium constituted by silica or glass doped with erbium ions, the saturable absorbent being constituted by silica or glass doped with uranium (U) ions or erbium (Er) ions,
   means for producing a signal ($S_1$) representative of a second radiation scattered by said gas, in response to the interaction between the molecules or atoms of gas and the first radiation.

4. Remote gas detection apparatus comprising:
   a first frequency tripled or quadrupled switched microlaser emitting a first radiation at a first wavelength ($\lambda_1$), comprising a saturable absorbent for passively switching the microlaser, and having an active laser medium constituted by silica or glass doped with erbium ions, the saturable absorbent being constituted by silica or glass doped with uranium (U) ions or erbium (Er) ions,
   means for producing a signal ($S_1$) representative of a second radiation scattered by said gas, in response to the interaction between the molecules or atoms of gas and the first radiation.

* * * * *